(12) United States Patent
Watson

(10) Patent No.: US 10,327,966 B2
(45) Date of Patent: Jun. 25, 2019

(54) DIAPER HAVING TOP EDGE TAB

(71) Applicant: Scottie Watson, Quincy, IL (US)

(72) Inventor: Scottie Watson, Quincy, IL (US)

( * ) Notice: Subject to any disclaimer, the term of this patent is extended or adjusted under 35 U.S.C. 154(b) by 93 days.

(21) Appl. No.: 15/217,043

(22) Filed: Jul. 22, 2016

(65) Prior Publication Data
US 2018/0021189 A1    Jan. 25, 2018

(51) Int. Cl.
| A61F 13/15 | (2006.01) |
| A61F 13/56 | (2006.01) |
| A61F 13/49 | (2006.01) |
| A61F 13/84 | (2006.01) |

(52) U.S. Cl.
CPC .... A61F 13/5622 (2013.01); A61F 13/49011 (2013.01); A61F 13/84 (2013.01)

(58) Field of Classification Search
CPC .................. A61F 13/5622; A61F 13/49014
USPC .................. 604/385.24, 385.29, 396, 385.3
See application file for complete search history.

(56) References Cited

U.S. PATENT DOCUMENTS

| 3,794,038 A | 2/1974 | Buell |
| 3,900,031 A | 8/1975 | D et al. |
| 4,055,182 A | 10/1977 | Mack |
| 4,337,771 A | 7/1982 | Pieniak et al. |
| 4,568,344 A | 2/1986 | Suzuki et al. |
| 4,604,096 A | 8/1986 | Dean et al. |
| 4,880,421 A | 11/1989 | Widlund |
| 5,690,627 A * | 11/1997 | Clear ................. A61F 13/15593 604/385.29 |
| 5,695,488 A | 12/1997 | Sosalla |
| 6,083,212 A * | 7/2000 | Kumasaka ............ A61F 13/496 604/358 |
| 6,138,282 A * | 10/2000 | Follese .................... A41B 9/14 2/220 |
| 6,210,386 B1 * | 4/2001 | Inoue ................. A61F 13/49011 604/385.01 |
| 2005/0027274 A1 * | 2/2005 | Suzuki .............. A61F 13/49001 604/385.01 |
| 2006/0047260 A1 * | 3/2006 | Ashton ................. A61F 13/496 604/396 |

* cited by examiner

*Primary Examiner* — Jacqueline F Stephens
(74) *Attorney, Agent, or Firm* — The Iwashko Law Firm, PLLC; Lev Ivan Gabriel Iwashko

(57) ABSTRACT

A modified diaper for allowing its top edge to be pulled back without placing one's finger inside the diaper. The modified diaper includes a diaper base that includes an edge tab. The diaper base defines a conventional disposable baby diaper. The edge tab defines an exterior flap which extends around the circumference of a top edge of the diaper base to form a finger slot that extends from around the entire exterior circumference of the diaper base. A user can insert their finger into this finger slot in order to pull the adjacent section of the top edge of the diaper base, and the portions of the diaper base adjacent to that top edge section, away from the waist of a wearer of the modified diaper without needing to stick their finger into the area between the wearer and the modified diaper.

2 Claims, 2 Drawing Sheets

DIAPER HAVING TOP EDGE TAB

BACKGROUND OF THE INVENTION

Field of the Invention

This invention relates generally to diapers and, more particularly, to a diaper having a reinforced top edge for use as an exterior pull back tab.

Description of the Prior Art

The use and design of baby diapers for absorbing or containing human waste to prevent soiling of clothing or other environmental items is well known. A problem which still exists, however, checking to see if a diaper has been soiled and needs changing often requires that a caretaker reach into a waistband to pull it away from the child's waist and visually inspect inside the diaper. When the diaper has been soiled with fecal matter, such an action often results in the caretaker getting the fecal on their hand and potentially spreading it along the child's back (as they remove their hand from in the waistband). Thus, there remains a need for a diaper having top edge tab which would a user to pull a waistband away from a child's waist with a finger (or thumb) without reaching inside the diaper. It would be helpful if such a diaper having top edge tab included reinforcing connectors for added strength when being pulled. It would be additionally desirable for such a diaper having top edge tab to have an elastic portion to reduce the chance of it sliding off the user's finger when pulled.

The Applicant's invention described herein provides for a wheeled diaper having top edge tab adapted to allow a user pull the waistband of a fastened diaper away from the waste of the wearer without reaching inside the diaper. The primary components in Applicant's diaper having top edge tab are a diaper base and an edge tab. When in operation, the diaper having top edge tab enables a caretaker to visually inspect inside a diaper without risk of soiling their hand. As a result, many of the limitations imposed by prior art structures are removed.

SUMMARY OF THE INVENTION

A modified diaper for allowing its top edge to be pulled back without placing one's finger inside the diaper. The modified diaper comprises a diaper base that includes an edge tab. The diaper base defines a conventional disposable baby diaper. The edge tab defines an exterior flap which extends around the circumference of a top edge of the diaper base to form a finger slot that extends from around the entire exterior circumference of the diaper base. A user can insert their finger into this finger slot in order to pull the adjacent section of the top edge of the diaper base, and the portions of the diaper base adjacent to that top edge section, away from the waist of a wearer of the modified diaper without needing to stick their finger into the area between the wearer and the modified diaper.

In one embodiment, the modified diaper additionally includes a plurality of reinforcing connectors positioned in the area between the edge tab and the exterior surface of the diaper base.

It is an object of this invention to provide a diaper having top edge tab which would a user to pull a waistband away from a child's waist with a finger (or thumb) without reaching inside the diaper.

It is another object of this invention to provide a diaper having top edge tab which includes reinforcing connectors for added strength when being pulled.

It is yet another object of this invention to provide a diaper having top edge tab that has an elastic portion to reduce the chance of it sliding off the user's finger when pulled.

These and other objects will be apparent to one of skill in the art.

DETAILED DESCRIPTION OF THE INVENTION

Figure 1:
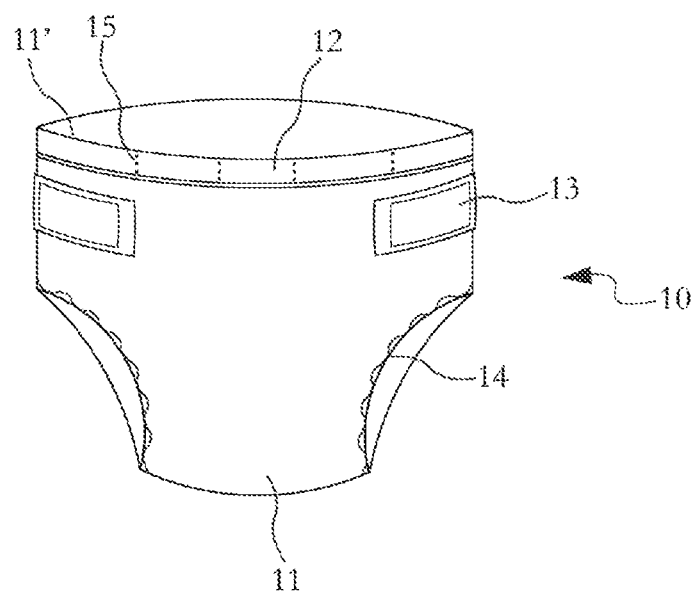
FIG. 1 is a front perspective view of a diaper having top edge tab built in accordance with the present invention.
Figure 2:
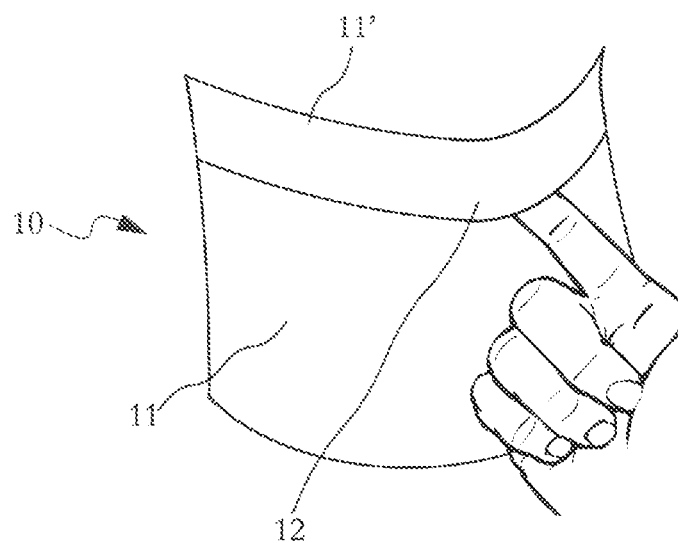
FIG. 2 is a front elevational view of a diaper having top edge tab built in accordance with the present invention shown with a finger engaging the top edge tab.

Referring now to the drawings and in particular FIGS. 1 and 2, a diaper having top edge tab (or "modified diaper") 10 is shown having a diaper base 11 that includes an edge tab 12. In one embodiment, the diaper base 11 defines a conventional disposable baby diaper that includes resealable sealing tapes 13 and elasticated leg cuffs 14. As such, it is contemplated that the diaper base 11 is adapted to absorb and/or contain human waste to prevent soiling of clothing or other environmental items as conventional diapers. It is appreciated that the diaper base 11 may be constructed in a plurality of sizes.

The edge tab 12 defines an exterior (relative to the diaper base 11) flap which extends from the top edge 11' of the diaper base 11. While the top of the edge tab 12 is connected to the diaper base 11 around the circumference of the top edge 11' of the diaper base 11, the bottom of the edge tab 12 does not connect to the diaper base 11. As such, a finger slot that extends from the bottom of the edge tab 12 to the top edge 11' of the diaper base 11 is formed in between the edge tab 12 and the exterior surface of the diaper base 11 around the entire exterior circumference of the diaper base 11. As illustrated in FIG. 2, a user can insert their finger into this finger slot in order to pull the top edge 11' of the diaper base 11 and the portions of the diaper base 11 adjacent to the top edge 11' away from the waist of a wearer of the modified diaper 10 without needing to stick their finger into the area between the wearer and the modified diaper 10.

In one embodiment, the modified diaper 10 additionally includes a plurality of reinforcing connectors 15 positioned in the area between the edge tab 12 and the exterior surface of the diaper base 11. The reinforcing connectors 15 operate to provide supplemental connection points that increase the strength of the attachment between the edge tab 12 and the exterior surface of the diaper base 11 at various locations around the circumference of the diaper base 11. In this regard, pulling force placed in the edge tab 12 more readily transfers to the top edge 11' and area of the diaper base 11 below the top edge 11'. In one embodiment, each reinforcing connectors 15 defines an attachment between the edge tab 12 and the exterior surface of the diaper base 11 formed by stitching. In another embodiment, each reinforcing connectors 15 defines an attachment between the edge tab 12 and the exterior surface of the diaper base 11 formed an adhesive.

In one embodiment, the edge tab 12 is constructed of an elastic material so that it can stretch when a user places their finger in the finger slot and pulls. Advantageously, such stretching allows for the user's finger to be held more securely in the finger slot.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A modified diaper, comprising:
   a diaper base adapted to at least contain human waste, wherein said diaper base includes an exterior surface and a top edge;
   an edge tab having a top end and a flap portion, wherein said top end is integral with said top edge and said flap portion extends over a portion of the exterior surface so as to form a finger slot between the edge tab and the exterior surface of the diaper base; and
   a plurality of reinforcing connectors disposed to be spaced apart from each other at predetermined distances along a circumference of the diaper base and through the finger slot and attached to the both edge tab and the exterior surface of the diaper base such that portions of the flap portion at each of the plurality of reinforcing connectors are fixed to the exterior surface of the diaper base.

2. The modified diaper of claim 1, wherein said flap portion includes elastic material.

* * * * *